(12) United States Patent
Stayman et al.

(10) Patent No.: US 12,097,055 B2
(45) Date of Patent: Sep. 24, 2024

(54) OPTIMAL SCAN PATTERN FOR MEDICAL IMAGING DEVICE

(71) Applicant: The Johns Hopkins University, Baltimore, MD (US)

(72) Inventors: Joseph Webster Stayman, Baltimore, MD (US); Jianan Gang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 333 days.

(21) Appl. No.: 17/753,726

(22) PCT Filed: Sep. 25, 2020

(86) PCT No.: PCT/US2020/052750
§ 371 (c)(1),
(2) Date: Mar. 11, 2022

(87) PCT Pub. No.: WO2021/062173
PCT Pub. Date: Apr. 1, 2021

(65) Prior Publication Data
US 2022/0338819 A1    Oct. 27, 2022

Related U.S. Application Data

(60) Provisional application No. 62/907,439, filed on Sep. 27, 2019.

(51) Int. Cl.
*G06K 9/00* (2022.01)
*A61B 6/00* (2006.01)
(Continued)

(52) U.S. Cl.
CPC ........... *A61B 6/032* (2013.01); *A61B 6/54* (2013.01); *G16H 30/20* (2018.01)

(58) Field of Classification Search
CPC .......... A61B 6/54; A61B 6/032; A61B 6/488; A61B 6/545
See application file for complete search history.

(56) References Cited

U.S. PATENT DOCUMENTS

| 11,348,243 B2 * | 5/2022 | Li ......................... G06T 7/0014 |
| 2011/0222648 A1 | 9/2011 | Tischenko et al. |

(Continued)

OTHER PUBLICATIONS

International Search Report and Written Opinion issued in Application No. PCT/US2020/052750; Dated Dec. 16, 2020, 6 Pages.
(Continued)

*Primary Examiner* — Hadi Akhavannik
(74) *Attorney, Agent, or Firm* — Harrity & Harrity, LLP

(57) ABSTRACT

In some implementations, a device may obtain scan information associated with scanning a section of a body that includes an object within tissue of the section. The device may determine a region of the section that is likely to be represented by an artifact in an image obtained using a first scanning type of a medical image device. The device may determine a plurality of scan patterns for scanning the region using a second scanning type. The device may determine, for the plurality of scan patterns, individual scan scores associated with scanning the region. The device may select, based on the individual scan scores, an optimal scan pattern from the plurality of scan patterns. The device may transmit the optimal scan pattern to the medical imaging device to permit the medical imaging device to scan the section to obtain optimized image data associated with the region.

20 Claims, 8 Drawing Sheets

(51) Int. Cl.
  *A61B 6/03* (2006.01)
  *G16H 30/20* (2018.01)

(56) References Cited

U.S. PATENT DOCUMENTS

| | | | |
|---|---|---|---|
| 2013/0142308 A1* | 6/2013 | Ishii | A61B 6/488 |
| | | | 378/62 |
| 2014/0148685 A1* | 5/2014 | Liu | A61B 6/542 |
| | | | 378/8 |
| 2015/0199478 A1* | 7/2015 | Bhatia | G06T 5/00 |
| | | | 382/128 |
| 2019/0198156 A1 | 6/2019 | Madani et al. | |
| 2022/0139529 A1* | 5/2022 | Bhatia | G16H 30/20 |
| | | | 382/131 |
| 2022/0338819 A1* | 10/2022 | Stayman | A61B 6/545 |

OTHER PUBLICATIONS

Tuy H.K., "An Inversion Formula for Cone-Beam Reconstruction," SIAM Journal on Applied Mathematics, Jun. 1983, vol. 43(3), 7 pages.

* cited by examiner

OPTIMAL SCAN PATTERN FOR MEDICAL IMAGING DEVICE

CROSS-REFERENCE TO RELATED APPLICATION

This Patent Application is a 371 national stage of PCT Application PCT/US2020/052750 filed on Sep. 25, 2020, entitled "OPTIMAL SCAN PATTERN FOR MEDICAL IMAGING DEVICE," which claims priority to United States Provisional Patent Application No. 62/907,439, filed on Sep. 27, 2019, and entitled "NON-CIRCULAR ORBIT FOR COMPUTED TOMOGRAPHY IMAGING DEVICE," both of which are hereby expressly incorporated by reference herein.

GOVERNMENT LICENSE RIGHTS

This invention was made with Government support under EB027127 awarded by the National Institutes of Health. The Government has certain rights in the invention.

BACKGROUND

A computed tomography (CT) imaging device uses computer-processed combinations of X-ray measurements taken from a variety of angles to produce cross-sectional images of specific areas of a scanned object (e.g., a section of a patient's body), allowing a user to obtain internal images of the object. CT imaging devices in the medical field are used to obtain internal images of a patient in order to diagnose, monitor, and/or treat a disease of the patient, an injury to the patient, and/or the like. Cone beam CT is an imaging technique that involves obtaining internal images of an object using divergent X-ray measurements in the form of a cone.

SUMMARY

In some implementations, a method includes obtaining image data associated with an image of a section of a body, wherein the image data is obtained via a scout scan of the section that is performed by a medical image device; analyzing the image data to identify an object within the section; determining, based on a position of the object as depicted in the image, a region of the section that is likely represented by an artifact in the image that is associated with the object; determining, based on the region of the artifact, a plurality of scan patterns for scanning the region; determining, for the plurality of scan patterns, individual scan scores associated with scanning the region, wherein an individual scan score, of the individual scan scores, indicates a level of coverage of a scan pattern associated with the individual scan score; selecting, based on the individual scan scores, an optimal scan pattern from the plurality of scan patterns; and causing the medical imaging device to perform a subsequent scan of the section according to the optimal scan pattern to obtain an optimal image of the region that is associated with a reduction or removal of the artifact.

In some implementations, a non-transitory computer-readable medium storing a set of instructions includes one or more instructions that, when executed by one or more processors of a device, cause the device to: obtain object information associated with an object positioned within a section of a body that is to be scanned by a medical imaging device, wherein the object information includes an object characteristic associated with the object; determine, based on the object characteristic, a region associated with the object that is likely to be represented by an artifact in an image generated by the medical imaging device according to the medical imaging device using a circular trajectory scan; determine, based on the region and information associated with the medical imaging device, a plurality of scan patterns associated with non-circular trajectory scans; select, based on individual scan scores of the plurality of scan patterns, an optimal scan pattern from the plurality of scan patterns, wherein a scan score of the individual scan scores, is associated with a predicted severity of the artifact that is generated according to a corresponding scan pattern used to scan the region; and perform an action associated with scanning the section using the optimal scan pattern to obtain an image of the region.

In some implementations, a device includes one or more memories; and one or more processors, communicatively coupled to the one or more memories, configured to: obtain scan information associated with scanning a section of a body that includes an object within tissue of the section; determine, based on the scan information, a region of the section that is likely to be represented by an artifact in an image obtained using a first scanning type of a medical image device; determine, based on the region of the artifact, a plurality of scan patterns for scanning the region using a second scanning type; determine for the plurality of scan patterns, individual scan scores associated with scanning the region; select, based on the individual scan scores, an optimal scan pattern from the plurality of scan patterns; and transmit the optimal scan pattern to the medical imaging device to permit the medical imaging device to scan the section to obtain optimized image data associated with the region.

DETAILED DESCRIPTION

Figure 1A:
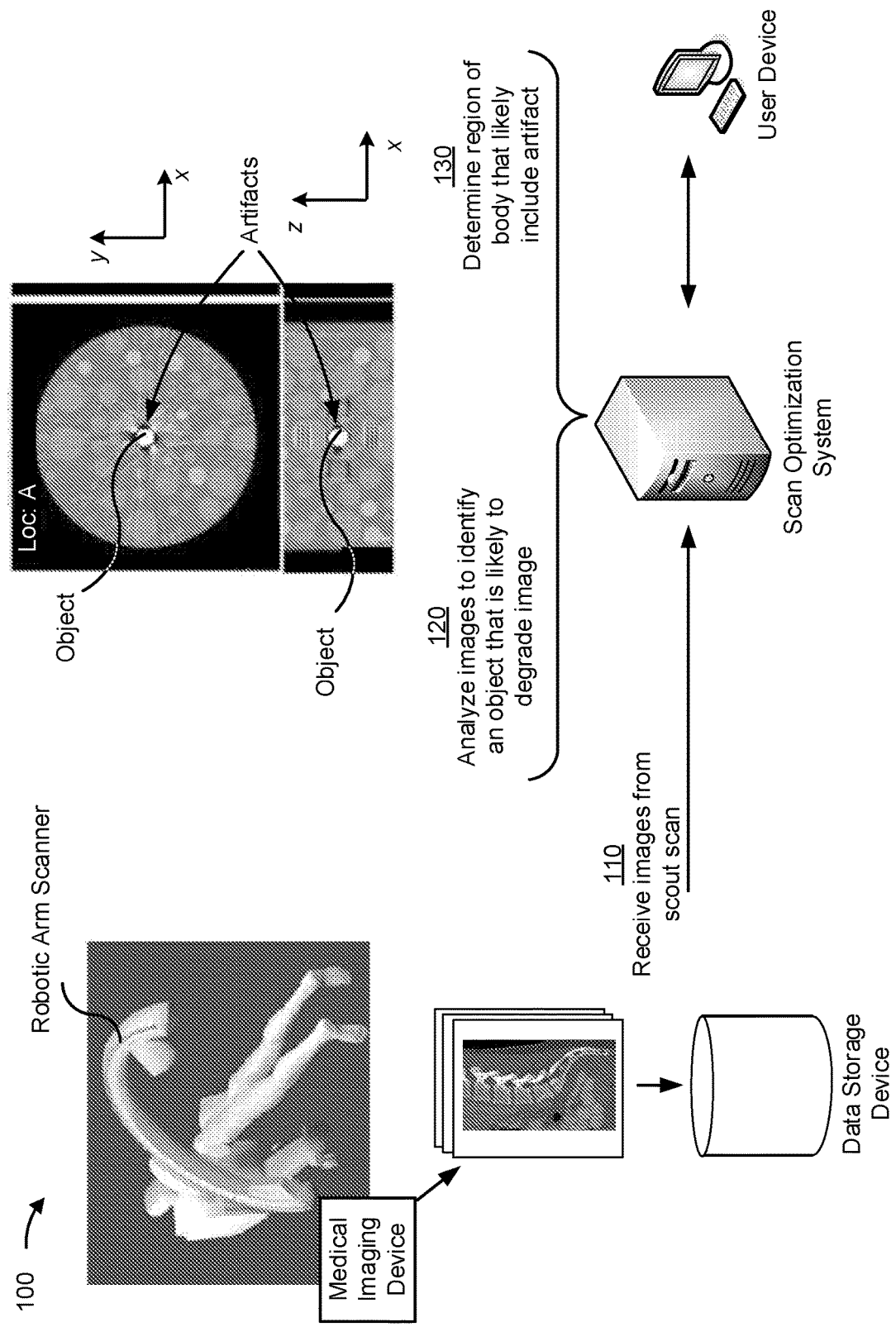
FIGS. 1A-1C are diagrams of an example implementation described herein.

The following detailed description of example implementations refers to the accompanying drawings. The same reference numbers in different drawings may identify the same or similar elements.

Artifacts may occur in diagnostic and image-guided cone beam computed tomography (CT) procedures due to the presence of objects, especially metal objects. For example, surgical tools and/or surgical hardware including embolization materials, dental fillings, artificial joints, fixation hardware, and/or the like cause artifacts to appear in CT images of a patient's body. More specifically, metal objects cause photon starvation and/or beam hardening which can appear in a depicted CT image as a bright artifact or dark artifact that confounds visualization of anatomical features surrounding the metal objects. Such an artifact can be especially severe when multiple metal objects are present, and can cause anatomical features positioned in between the metal objects to be obfuscated (and/or completely obliterated). Previous algorithmic solutions involve attempting to mitigate or reduce the severity of obfuscation to produce a visually acceptable image by replacing an artifact with artificially generated image data (which may reduce an appearance of streaks of the artifacts, but cannot accurately represent the internal structure of the patient). In some instances, image corrections interpolate over regions associated with the artifact in the projection data, effectively treating those projections as missing data. However, without additional prior information associated with the region (e.g., obtained from an image captured prior to placement or insertion of the object), there is no way to guarantee accurate interpolations of the missing information.

According to some implementations described herein, an imaging system may determine and use a non-circular orbit to avoid artifacts (e.g., associated with or caused by an object) according to a design of scan pattern (of a plurality of trajectories) of a scanner of the imaging system. As described herein, an imaging system may be configured to find a data solution by applying a model (e.g., a Tuy model) to obtain complete image data correspondingly. For example, because metal implants may effectively cause beam hardening, photon starvation, and/or missing data in images (or projections of the images), an optimal scan pattern (e.g., corresponding to an orbital design of a trajectory of the scanner) for an imaging system can be configured that will reduce and/or eliminate potential missing data or an appearance of an artifact in an image based on a position of the object within the imaging field-of-view. Such scan patterns can be used to control an imaging device to capture images in corresponding trajectories (which may include non-circular orbits of the scanner). The resulting scan patterns can be highly robust to metal objects and provide improved visualization of features (e.g., anatomical features) that are ordinarily obscured according to previous techniques.

In some implementations, an imaging device (e.g., a medical imaging device that includes a CT scanner mounted to a robotic arm) is capable of general source-detector trajectories. Specifically, while standard CT data acquisition uses a single circular orbit or a plurality of circular orbits (e.g., partially circular orbit, offset or combined semicircular orbits, a helical orbit, and/or the like), some implementations described herein use generalized trajectories for improved CT image quality. In particular, the issue of metal artifacts in CT images is addressed by designing scan patterns that are tolerant to metal objects in a field-of-view of the CT scanner (e.g., to produce artifact-free or nearly artifact-free images). The example imaging device may utilize a modern robotic C-arm system. In some implementations, the imaging system may consider one or more characteristics and/or capabilities of the imaging device to optimize the design of a scan pattern for a particular section of a patient's body and/or minimize the appearance or presence of artifacts in images of the section of the patient's body.

Accordingly, as described herein, based on one or more characteristics of an object in a section of a patient's body, through the use of an analysis that determines and/or quantifies a severity of an artifact (e.g., a size of a region associated with Tuy's condition on completeness or data redundancy) one can reduce or minimize both the missing or inaccurate data associated with the artifact that is introduced by the metal, and subsequent artifacts. In this way, such an imaging system enables enhanced accuracy in analyzing and/or diagnosing a characteristic of a particular individual or health condition depicted in the images, thus correspondingly conserving computing resources (which may be spent based on inaccurate imaging and/or attempting to address inaccurate imaging) and/or reducing the risk of misdiagnosing and/or treating a patient based on inaccurate images or missing information.

Figure 1B:
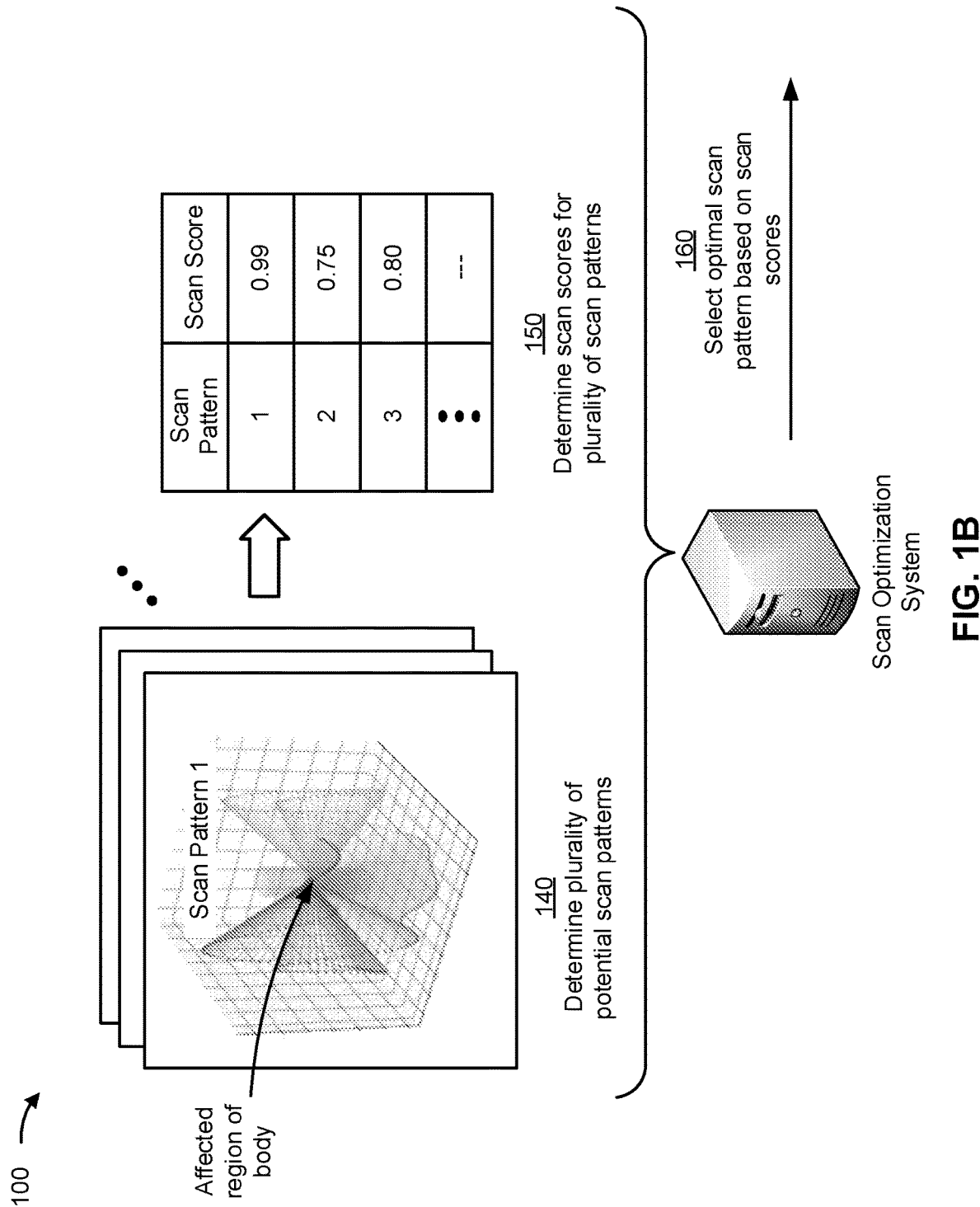
Figure 1C:
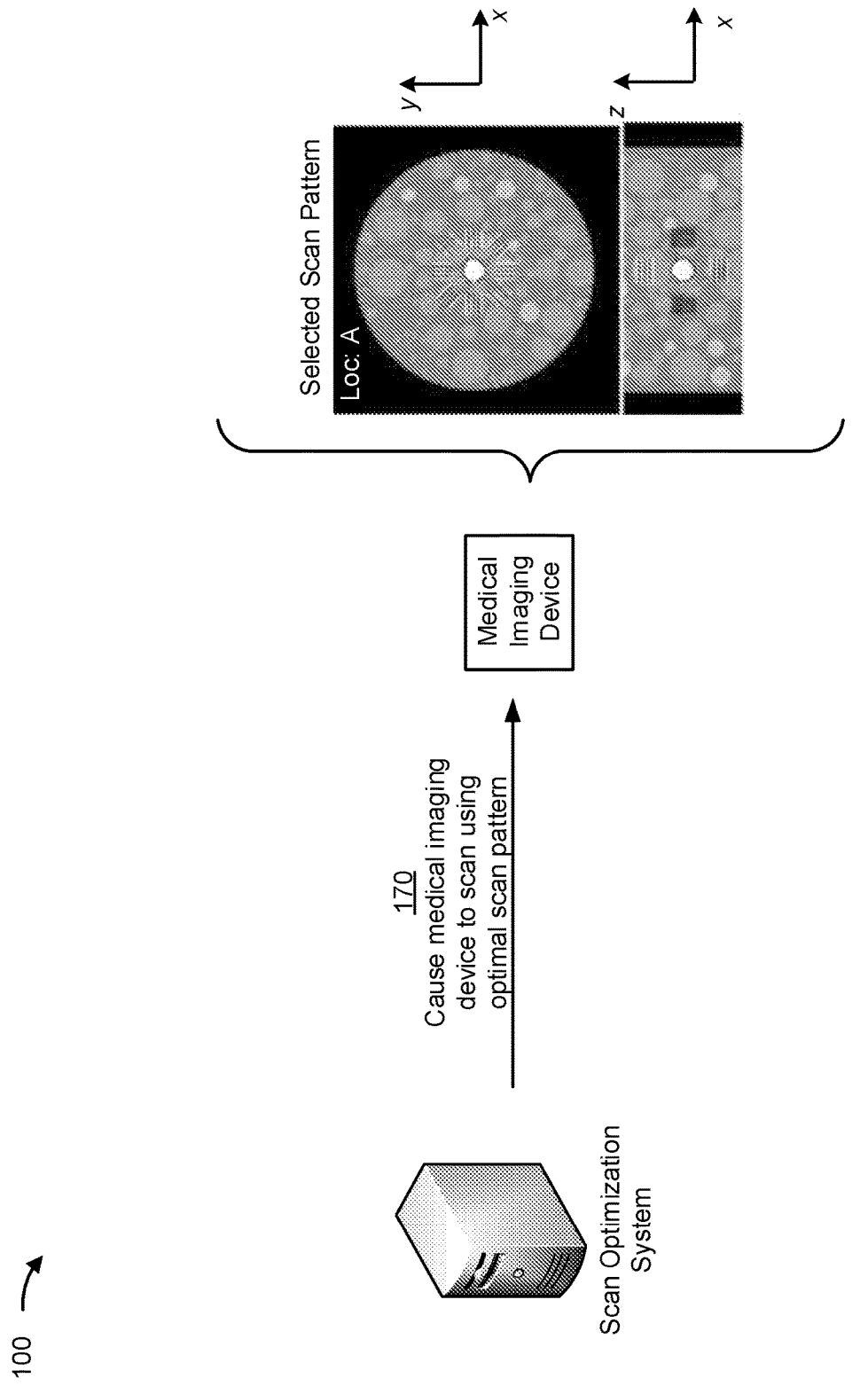

FIGS. 1A-1C are diagrams of an example 100 associated with an optimal scan pattern for a medical imaging device. As shown in FIGS. 1A-1C, example 100 includes a scan optimization system, a data storage device, and a user device. According to some implementations, the scan optimization system determines an optimal scan pattern (e.g., relative to a model and/or function described herein) for a section of a body of a patient to mitigate and/or reduce a severity of an artifact caused by one or more objects within the section. Additionally, or alternatively, the scan optimization system may cause and/or permit the medical imaging device to perform the optimal scan.

Although, in example 100, the object may be referred to a metal object or an object that causes a metal artifact, the object may correspond to any object that can cause an artifact to appear in an image associated with a scan plane of a scan of the medical imaging device. Accordingly, the object may include any type of foreign object, such as surgical hardware (e.g., screws, plates, rods, and/or the like), surgical tools, or non-surgical related objects (e.g., objects received within the body due to impalement, ingestion, and/or the like). In some implementations, the object may correspond to certain anatomical objects, such as bone, certain tissue (e.g., tumor tissue), and/or the like that cause artifacts.

As shown in FIG. 1A, and by reference number 110, the scan optimization system receives images from a scout scan of a patient. The scout scan may be performed to detect and/or identify, from the images, an object in a section of the patient's body. In example 100, the medical imaging device includes a scanner that is mounted to a robotic arm (e.g., a C-arm of a CT imaging device). The scout scan may be performed using a circular scan pattern that includes the scanner moving in a plurality of ring trajectories and/or the scanner moving in one or more helix trajectories. Additionally, or alternatively, the scout scan may be performed using one or more other patterns that can identify the location of an object (e.g., two or more projection view scout scans). As described herein, the scout scan may be performed to determine object information from an analysis of the image data.

The image data may include and/or be associated with one or more images of a section of the patient's body. The images may be captured and/or provided (e.g., to the data storage device) by the medical imaging device and/or received from a data storage device. The data storage device may be associated with (e.g., communicatively coupled with, installed within, and/or the like) the medical imaging device, the user device, and/or the scan optimization system. The images and/or image data may be associated with a CT scan (e.g., obtained from a CT scan device), a magnetic resonance imaging (MRI) scan, an X-ray scan, and/or the like.

According to some implementations, the scan optimization system may receive the images as image data (e.g., data that can be used to render the images, projection data, and/or the like). In some implementations, the image data may be representative of a plurality (or series) of images of the patient and/or of a specific section of the patient's body. Additionally, or alternatively, the image data may correspond to a three-dimensional (3D) graphical representation of the section that includes the object.

In this way, the scan optimization system may receive image data associated with images of a section of a body and/or an object within the section to permit the scan optimization system to determine an optimal scan pattern for scanning the section to reduce a severity of an artifact caused by the object.

As further shown in FIG. 1A, and by reference number 120, the scan optimization system analyzes the image data to identify an object that is likely to degrade the image. For example, based on receiving image data and/or a request for an optimal scan pattern (e.g., from the user device), the scan optimization system may analyze the image data (e.g., pixel values and/or voxel values) to identify the object.

According to some implementations, one or more artificial intelligence techniques, including machine learning, deep learning, neural networks, and/or the like can be used to detect and/or identify an object in the images and correspondingly, within the section of the body. For example, the scan optimization system may use a computer vision technique, such as a convolutional neural network technique, to assist in classifying image data (e.g., image data including representations of objects within the patient and/or the like) into a particular class. More specifically, the scan optimization system may determine that an object (e.g., an object associated with causing an artifact) has a particular characteristic (e.g., is a certain type of material, has a certain shape, has a certain size, and/or the like). On the other hand, the scan optimization system may determine that an object (e.g., an object that doesn't cause an artifact) does not have a particular characteristic. Furthermore, the scan optimization system may be configured to analyze image data to determine whether an object represented in the image data is associated with causing and/or generating an artifact in an image of the imaging device.

In some implementations, the computer vision technique and/or an image processing technique described herein may include using an image recognition technique (e.g., an Inception framework, a ResNet framework, a Visual Geometry Group (VGG) framework, and/or the like), an object detection technique (e.g. a Single Shot Detector (SSD) framework, a You Only Look Once (YOLO) framework, a cascade classification technique (e.g., a Haar cascade technique, a boosted cascade, a local binary pattern technique, and/or the like), and/or the like), an edge detection technique, and/or the like. Additionally, or alternatively, the computer vision technique and/or image processing technique may be configured to analyze particular anatomical features of an individual (or patient) (e.g., based on which section of the patient's body is being scanned). For example, the computer vision technique and/or image processing technique may be configured to identify certain bone structures, certain types of tissue (e.g., organ tissue, skin tissue, muscle tissue, fat tissue, and/or the like), and/or the like. In some implementations, the computer vision technique and/or the image processing technique is specifically configured to identify certain objects (e.g., certain types of objects in images). For example, the image processing technique may identify the objects based on pixel values that are used to depict the one or more types of objects (e.g., to identify a particular material of the object, such as metal, plastic, and/or the like), shapes of the one or more types of objects, sizes of the one or more types of objects, and/or the like.

In this way, the scan optimization system may analyze the images to detect and/or identify an object (or multiple objects) within a section of a body to permit the scan optimization system to determine regions that include (or likely include) an artifact caused by the object.

As further shown in FIG. 1A, and by reference number 130, the scan optimization system determines a region of the body that likely includes an artifact. The region of the body may correspond to a region of the section of the body represented by the images that depict the object and may correspond to pixels and/or voxels of the artifact. The scan optimization system may determine the region (e.g., locations of the region, a size of the region, a shape of the region) based on a location of the object within the section of the body. In some implementations, the scan optimization system may determine the location of the object within the body based on pixel coordinates and/or voxel coordinates associated with the object as depicted in the images. In some implementations, the region may correspond to a portion of the body section that is within a distance threshold of the object (e.g., the region may correspond to a shell of anatomical features (bone, tissue, and/or the like) that surround the object.

In some implementations, the scan optimization system may use a machine learning model, such as an artifact region identification model, to determine the region of the body that likely includes an artifact caused by an object. For example, the artifact region identification model may include and/or utilize one or more of a neural network, a linear regression model, a computer vision model, and/or the like. The artifact region identification model may be trained using historical data that is associated with identifying artifacts in images based on historical values for one or more artifact identification parameters. Such artifact identification parameters may include one or more object characteristics (e.g., the location of the object, a size of the object, the shape of the object, the type of the object, and/or the like), anatomical characteristics of an anatomy adjacent or near the object (e.g., tissue type, which section or body part includes the object, image characteristics (e.g., image resolution, quantity of images, image type, and/or the like), scanner characteristics (e.g., scanner type, scanner settings, and/or the like), and/or the like. Correspondingly, the historical data may include historical images of bodies (and/or sections of bodies) that include one or more objects and artifacts generated and/or caused by the one or more objects.

Using the historical data and values determined for the one or more artifact identification parameters as inputs to the artifact identification model, the scan optimization system may determine the region of the body (or section of the body) that likely includes an artifact, to permit the scan optimization system to determine an optimal scan pattern to obtain more accurate image data associated with the region (e.g., to reduce the severity or impact of the artifact), as described herein. In some implementations, the scan optimization system may retrain and/or cause the artifact identification model to be retrained by updating the historical data to include validated or invalidated results associated with input values of the one or more artifact identification parameters.

According to some implementations, the scan optimization system may receive scan information associated with the medical imaging device performing a patient scan (e.g., associated with a request to determine an optimal scan of the section of the patient's body). The scan information may include object information associated with the object and/or body information associated with the body. For example, rather than determining the object information from a scout scan, the user (e.g., a doctor, patient, and/or the like) may indicate and/or input the object location via the user device and/or a user interface of the scan optimization system. The object information may include one or more of the object characteristics (e.g., a material of the object, a type of the object identified in the object information, a size of the object identified in the object information, a shape of the object identified in the object information, and/or the like). More specifically, the user may indicate a position (e.g., a location and/or orientation) of the object (e.g., relative to the section of the body and/or relative a trajectory range of the scanner) that can include the object. Additionally, or alternatively, the user may indicate body information indicating which section of the body (and/or which body part, bone, organ, tissue, and/or the like) is near and/or adjacent the object, a dimension of the section (e.g., length, width, depth, diameter, and/or the like of the section of the body or of the patient's body part associated with the section).

In this way, the scan optimization system may determine a region of the body that likely is associated with an artifact of an image (e.g., obtained from the scout scan) or likely to include an artifact if scanned using a circular trajectory.

As shown in FIG. 1B, and by reference number 140, the scan optimization system determines a plurality of potential scan patterns to scan the section of the body. For example, the scan optimization system may iteratively determine a quantity of scan patterns that each include a plurality of trajectories of the scanner. In some implementations, the scan optimization system may determine and/or generate a potential scan pattern to scan locations of the region using scan planes that do not include the object (e.g., so that the object does not prevent the scanner from accurately capturing image data for the locations of the region). As described herein, the potential scan patterns may include one or more trajectories (e.g., non-circular trajectories) that are different from the trajectories of the scout scan. In this way, one or more of the potential scan patterns can be used to produce an image that does not include the artifact or includes an artifact that is smaller and/or less severe than the images from the scout scan (and/or images using scan patterns with only circular trajectories). The quantity of scan patterns may be based on a desired level of accuracy, a desired duration of a scan, a desired speed of the scan, and/or the like. For example, a relatively higher quantity of scans may improve a likelihood of selecting an optimal scan pattern that provides the most scan coverage of the region without being blocked or impeded by the object, thereby reducing the size and/or severity of the artifact.

In some implementations, the scan optimization system may use a scan pattern configuration model that determines and/or generates scan patterns that cover one or more locations of the region. For example, the scan pattern configuration may use a sampling technique to select (e.g., from a set of preconfigured scan patterns and/or from a set of preconfigured trajectories of the scanner of the medical imaging device) potential scan patterns to determine which of the potential scan patterns corresponds to an optimal scan pattern (e.g., relative to the scan pattern configuration model and/or an optimization model associated with scanning the region via scan planes that do not intersect the object). In some implementations, the scan pattern configuration model may use one or more scanning parameters to determine potential scan patterns and/or trajectories of the potential scan patterns that can be used to scan the region to reduce the severity of the artifact. Such scanning parameters may include a position of the object (e.g., relative to the section of the body), characteristics of the section of the body (e.g., anatomical characteristics, dimensions of the section, body composition of the section, and/or the like). Additionally, or alternatively, such scanning parameters may include one or more characteristics of the scanner and/or capabilities of the medical imaging device. For example, such capabilities may be associated with physical limitations of a robotic arm and/or scanner of the medical imaging device, such as spatial constraints (e.g., spatial constraints associated with a room of the medical imaging device, such constraints caused by a layout of objects and/or positioning of individuals in an operating room or other room of the medical imaging device), movement constraints (e.g., velocity capabilities, acceleration capabilities, positioning ranges or capabilities, and/or the like), image capture capabilities, such as resolution range, speed capability (or frame rate), zoom capability, and/or the like). In some implementations, the scanning parameters may include one or more user preferences for a scan, such as a preferred angle or direction of a scan plane, a radioactive dosage threshold of the scan, a speed of the scan, a duration of the scan, and/or the like. According to some implementations, the scan pattern configuration model may use the scanning parameters to determine a sequence of trajectories of the scanner that can be combined and/or performed in a manner that satisfies one or more of the thresholds defined or associated with the scanning parameters.

According to some implementations, the scan optimization system may determine an optimal scan pattern for a region of a patient's body (or for a particular body part) regardless of whether a position of the object (or a likely location of an artifact caused by the object) is known to the scan optimization system. In such a case, the scan optimization system may determine the optimal scan pattern based on an indication (e.g., a binary indication) that the particular region includes an object. Furthermore, in such a case, the scan optimization system may determine the optimal scan pattern according to one or more of the physical limitations, body information of the patient (e.g., dimensions, type of body part in the region, and/or the like), movement constraints, image capture capabilities, user preferences, and/or the like. In this way, regardless of knowing a particular location of an object and/or an area of the object within a region of the body that is to be scanned, the scan optimization system may determine an optimal scan according to one or more parameters that do not include the location information associated with the object (or likely artifacts caused by the object).

In this way, the scan optimization system may determine a plurality of scan patterns that include non-circular trajectories (which may be referred to individually as a "non-circular trajectory scan") that can be used to provide an improved view of the region, thereby reducing the effects of the object and/or reducing a size of the artifact when the section is scanned according to one or more of the plurality of scan patterns.

As further shown in FIG. 1B, and by reference number 150, the scan optimization system determines scan scores of the plurality of scan patterns. For example, for each of the potential scan patterns that are generated and/or determined to satisfy one or more thresholds for an optimal scan of the section, the scan optimization system may determine a score of the potential scan patterns to determine which of the potential scan patterns corresponds to an optimal scan pattern (e.g., relative to the others). The individual scan scores may correspond to a level of coverage of a scan pattern associated with the individual scan score. For example, the scan scores may correspond to a percentage of locations of the region and/or locations of the section of the body that can be scanned by the corresponding scan patterns without the object being in at least one of the same scan planes that scans the locations.

According to some implementations, to determine a scan score for one of the potential scan patterns (or for each of the potential scan patterns), the scan optimization system may determine the locations of the region (e.g., corresponding to locations of pixels and/or voxels of the image data). The scan optimization system may identify a percentage of the locations that are included in at least one scan plane of the trajectory of the scan pattern that does not intersect the object (or a portion of the object). The percentage of the locations and/or a probability associated with the percentage of the locations being covered, as described herein, may be used to determine the scan score. Accordingly, a scan score may indicate an amount of the region that would be covered by a corresponding scan pattern without the object blocking scan planes that intersect locations of the region.

In this way, the scan optimization system may determine individual scan scores associated with the plurality of potential scans of the section and/or the region to permit the scan optimization system to select and/or identify an optimal scan for the section of the body relative to the position of the object.

As further shown in FIG. 1B, and by reference number 160, the scan optimization system selects an optimal scan pattern based on the scan scores. For example, the scan optimization system may compare the scan scores for the plurality of potential scan patterns and select the scan pattern that has a score associated with the scan pattern providing the most coverage of the region without being blocked by the object. Accordingly, the optimal scan pattern may be associated with a scan score that indicates that the optimal scan pattern would cause the scanner of the medical imaging device to move in trajectories that provide scan planes that cover a largest portion of the region, relative to the other potential scan patterns, without including the object.

In this way, the scan optimization system may determine an optimal scan pattern (e.g., relative to a scan pattern configuration model and/or relative to a particular set of potential scan patterns) that would cause the medical imaging device to generate image data without an artifact or with a smaller artifact than a scan pattern consisting of circular trajectories (e.g., ring trajectories and/or helix trajectories).

As shown in FIG. 1C, and by reference number 170, the scan optimization system causes the medical imaging device to scan (e.g., rescan after the scout scan) the section using the selected scan pattern. For example, the scan optimization system may provide and/or transmit instructions that include the optimal scan pattern to cause the medical imaging device to capture images with minimal artifacts or without artifacts, thereby providing relatively enhanced images of the section of the body.

In some implementations, the scan optimization system may provide (e.g., via a user interface of the scan optimization system and/or the user device) information associated with the optimal scan pattern. For example, the scan optimization system may provide the scan score and/or a characteristic of a scan performed according to the optimal scan pattern (e.g., a level of accuracy of images of the scan, a duration of the scan, a speed of the scan, a resolution of images of the scan, an estimated radiation dosage associated with the scan, and/or the like).

In this way, the scan optimization system may transmit the optimal scan pattern to the medical imaging device to cause the medical imaging device to perform a scan according to the optimal scan pattern, thereby providing relatively enhanced imagery of the section of the body and allowing for improved diagnosis of the patient. Furthermore, the scan optimization system, relative to previous scan techniques, may conserve computing resources that are spent relying on inaccurate images that include artifacts and may reduce the risk of misdiagnosing and/or mistreating a patient based on images that include artifacts as a result of the previous scan techniques.

As indicated above, FIGS. 1A-1C are provided as an example. Other examples may differ from what is described with regard to FIGS. 1A-1C. The number and arrangement of devices shown in FIGS. 1A-1C are provided as an example. In practice, there may be additional devices, fewer devices, different devices, or differently arranged devices than those shown in FIGS. 1A-1C. Furthermore, two or more devices shown in FIGS. 1A-1C may be implemented within a single device, or a single device shown in FIGS. 1A-1C may be implemented as multiple, distributed devices. Additionally, or alternatively, a set of devices (e.g., one or more devices) shown in FIGS. 1A-1C may perform one or more functions described as being performed by another set of devices shown in FIGS. 1A-1C.

Figure 2:
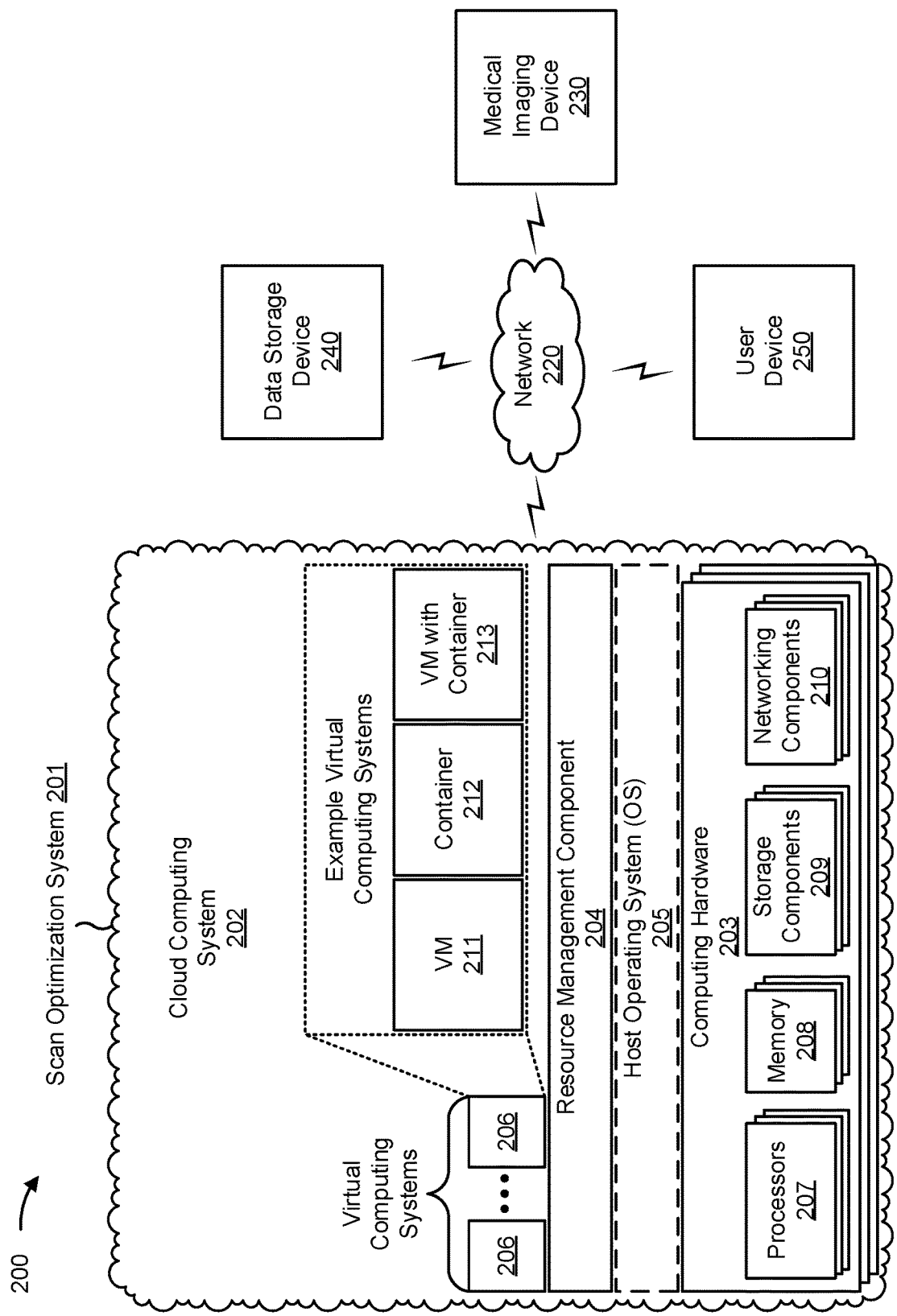
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a scan optimization system 201, which may include one or more elements of and/or may execute within a cloud computing system 202. The cloud computing system 202 may include one or more elements 203-213, as described in more detail below. As further shown in FIG. 2, environment 200 may include a network 220, a medical imaging device 230, a data storage device 240, and/or a user device 250. Devices and/or elements of environment 200 may interconnect via wired connections and/or wireless connections.

The cloud computing system 202 includes computing hardware 203, a resource management component 204, a host operating system (OS) 205, and/or one or more virtual computing systems 206. The resource management component 204 may perform virtualization (e.g., abstraction) of computing hardware 203 to create the one or more virtual computing systems 206. Using virtualization, the resource management component 204 enables a single computing device (e.g., a computer, a server, and/or the like) to operate like multiple computing devices, such as by creating multiple isolated virtual computing systems 206 from computing hardware 203 of the single computing device. In this way, computing hardware 203 can operate more efficiently, with lower power consumption, higher reliability, higher availability, higher utilization, greater flexibility, and lower cost than using separate computing devices.

Computing hardware 203 includes hardware and corresponding resources from one or more computing devices. For example, computing hardware 203 may include hardware from a single computing device (e.g., a single server) or from multiple computing devices (e.g., multiple servers), such as multiple computing devices in one or more data centers. As shown, computing hardware 203 may include one or more processors 207, one or more memories 208, one or more storage components 209, and/or one or more networking components 210. Examples of a processor, a memory, a storage component, and a networking component (e.g., a communication component) are described elsewhere herein.

The resource management component 204 includes a virtualization application (e.g., executing on hardware, such as computing hardware 203) capable of virtualizing computing hardware 203 to start, stop, and/or manage one or more virtual computing systems 206. For example, the resource management component 204 may include a hypervisor (e.g., a bare-metal or Type 1 hypervisor, a hosted or Type 2 hypervisor, and/or the like) or a virtual machine monitor, such as when the virtual computing systems 206 are virtual machines 211. Additionally, or alternatively, the resource management component 204 may include a container manager, such as when the virtual computing systems 206 are containers 212. In some implementations, the resource management component 204 executes within and/or in coordination with a host operating system 205.

A virtual computing system 206 includes a virtual environment that enables cloud-based execution of operations and/or processes described herein using computing hardware 203. As shown, a virtual computing system 206 may include a virtual machine 211, a container 212, a hybrid environment 213 that includes a virtual machine and a container, and/or the like. A virtual computing system 206 may execute one or more applications using a file system that includes binary files, software libraries, and/or other resources required to execute applications on a guest operating system (e.g., within the virtual computing system 206) or the host operating system 205.

Although the scan optimization system 201 may include one or more elements 203-213 of the cloud computing system 202, may execute within the cloud computing system 202, and/or may be hosted within the cloud computing system 202, in some implementations, the scan optimization system 201 may not be cloud-based (e.g., may be implemented outside of a cloud computing system) or may be partially cloud-based. For example, the scan optimization system 201 may include one or more devices that are not part of the cloud computing system 202, such as device 300 of FIG. 3, which may include a standalone server or another type of computing device. The scan optimization system 201 may perform one or more operations and/or processes described in more detail elsewhere herein.

Network 220 includes one or more wired and/or wireless networks. For example, network 220 may include a cellular network, a public land mobile network (PLMN), a local area network (LAN), a wide area network (WAN), a private network, the Internet, and/or the like, and/or a combination of these or other types of networks. The network 220 enables communication among the devices of environment 200.

Medical imaging device 230 includes one or more devices capable of receiving, generating, storing, processing, and/or providing information and/or images (e.g., pre-operative images, intra-operative images, and/or post-operative images, and/or the like). For example, medical imaging device 230 may include a CT scan device, a magnetic resonance imaging (MRI) device, an X-ray device, a positron emission tomography (PET) device, an ultrasound imaging (USI) device, a photoacoustic imaging (PAI) device, an optical coherence tomography (OCT) device, an elastography imaging device, and/or a similar type of device. In some implementations, medical imaging device 230 performs a scan according to an optimal scan pattern received from the scan optimization system 201. Additionally, or alternatively, medical imaging device 230 may generate and provide one or more images to scan optimization system 201 to cause or request scan optimization system 201 to determine and provide an optimized scan of a patient based on the images.

Data storage device 240 includes one or more devices capable of receiving, generating, storing, processing, and/or providing information associated with images (e.g., CT images) of a patient, image data associated with images of a patient, a scan pattern associated with scanning a patient, and/or the like. For example, in some implementations, data storage device 240 may include a server device, a hard disk device, an optical disk device, a solid-state drive (SSD), a compact disc (CD), a network attached storage (NAS) device, a flash memory device, a cartridge, a magnetic tape, and/or another device that can store and provide access to perioperative images, demographic data, patient outcome metrics, and/or the like.

User device 250 includes one or more devices capable of receiving, generating, storing, processing, and/or providing information associated with images of a patient, a scan of medical imaging device 230, one or more scan patterns for the medical imaging device 230, and/or the like. For example, user device 250 may include a communication and/or computing device, such as a laptop computer, a tablet computer, a handheld computer, a desktop computer, a surgical device, a mobile phone (e.g., a smart phone, a radiotelephone, and/or the like), a wearable communication device (e.g., a smart wristwatch, a pair of smart eyeglasses, and/or the like), or a similar type of device.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
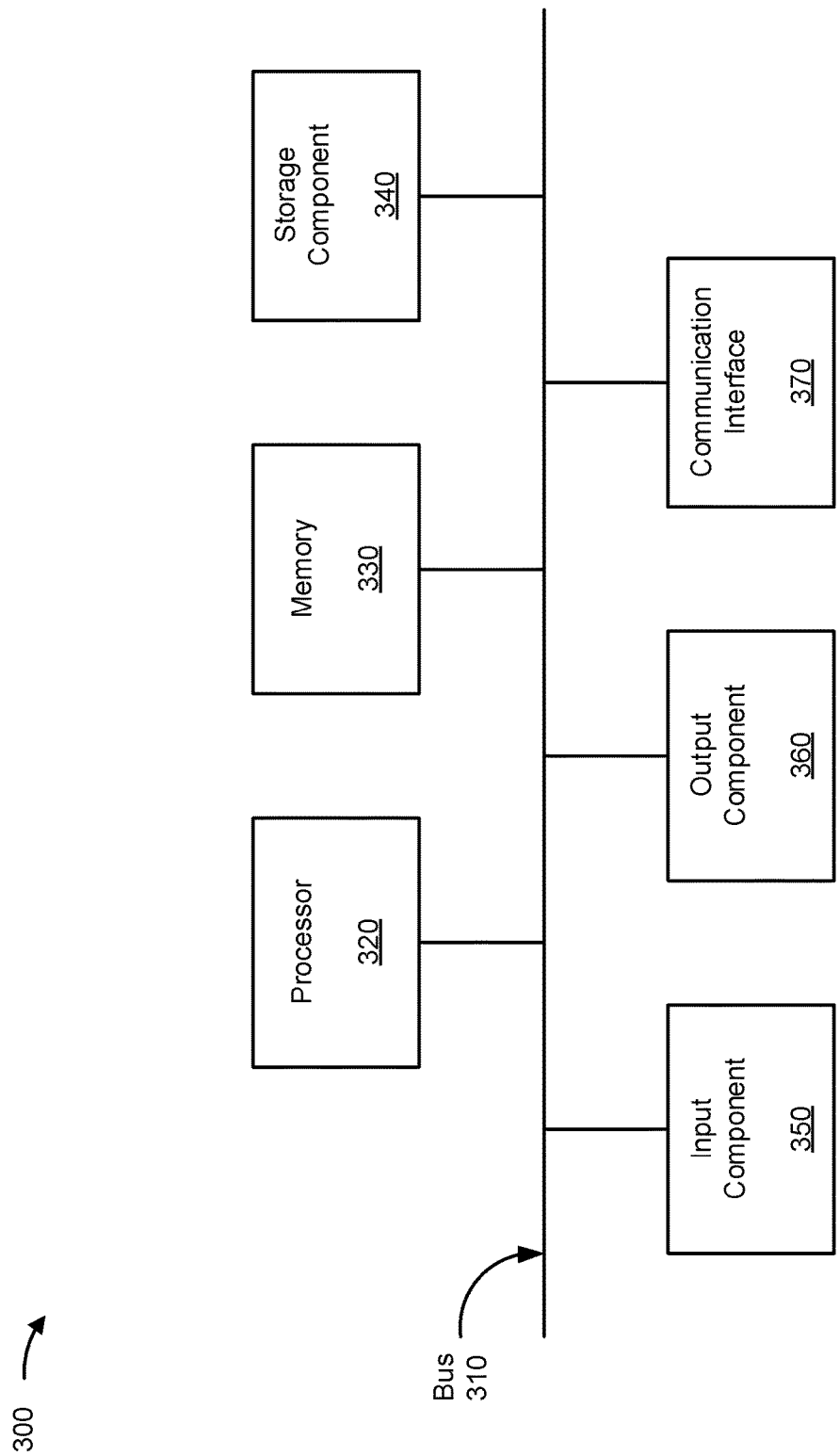
FIG. 3 is a diagram of example components of one or more devices of FIG. 2.

FIG. 3 is a diagram of example components of a device 300, which may correspond to components of scan optimization system 201, medical imaging device 230, and/or data storage device 240. In some implementations, components of scan optimization system 201, medical imaging device 230, and/or data storage device 240 may include one or more devices 300 and/or one or more components of device 300. As shown in FIG. 3, device 300 may include a bus 310, a processor 320, a memory 330, a storage component 340, an input component 350, an output component 360, and a communication component 370.

Bus 310 includes a component that enables wired and/or wireless communication among the components of device 300. Processor 320 includes a central processing unit, a graphics processing unit, a microprocessor, a controller, a microcontroller, a digital signal processor, a field-programmable gate array, an application-specific integrated circuit, and/or another type of processing component. Processor 320 is implemented in hardware, firmware, or a combination of hardware and software. In some implementations, processor 320 includes one or more processors capable of being programmed to perform a function. Memory 330 includes a random access memory, a read only memory, and/or another type of memory (e.g., a flash memory, a magnetic memory, and/or an optical memory).

Storage component 340 stores information and/or software related to the operation of device 300. For example, storage component 340 may include a hard disk drive, a magnetic disk drive, an optical disk drive, a solid state disk drive, a compact disc, a digital versatile disc, and/or another type of non-transitory computer-readable medium. Input component 350 enables device 300 to receive input, such as user input and/or sensed inputs. For example, input component 350 may include a touch screen, a keyboard, a keypad, a mouse, a button, a microphone, a switch, a sensor, a global positioning system component, an accelerometer, a gyroscope, an actuator, and/or the like. Output component 360 enables device 300 to provide output, such as via a display, a speaker, and/or one or more light-emitting diodes. Communication component 370 enables device 300 to communicate with other devices, such as via a wired connection and/or a wireless connection. For example, communication component 370 may include a receiver, a transmitter, a transceiver, a modem, a network interface card, an antenna, and/or the like.

Device 300 may perform one or more processes described herein. For example, a non-transitory computer-readable medium (e.g., memory 330 and/or storage component 340) may store a set of instructions (e.g., one or more instructions, code, software code, program code, and/or the like) for execution by processor 320. Processor 320 may execute the set of instructions to perform one or more processes described herein. In some implementations, execution of the set of instructions, by one or more processors 320, causes the one or more processors 320 and/or the device 300 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 3 are provided as an example. Device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
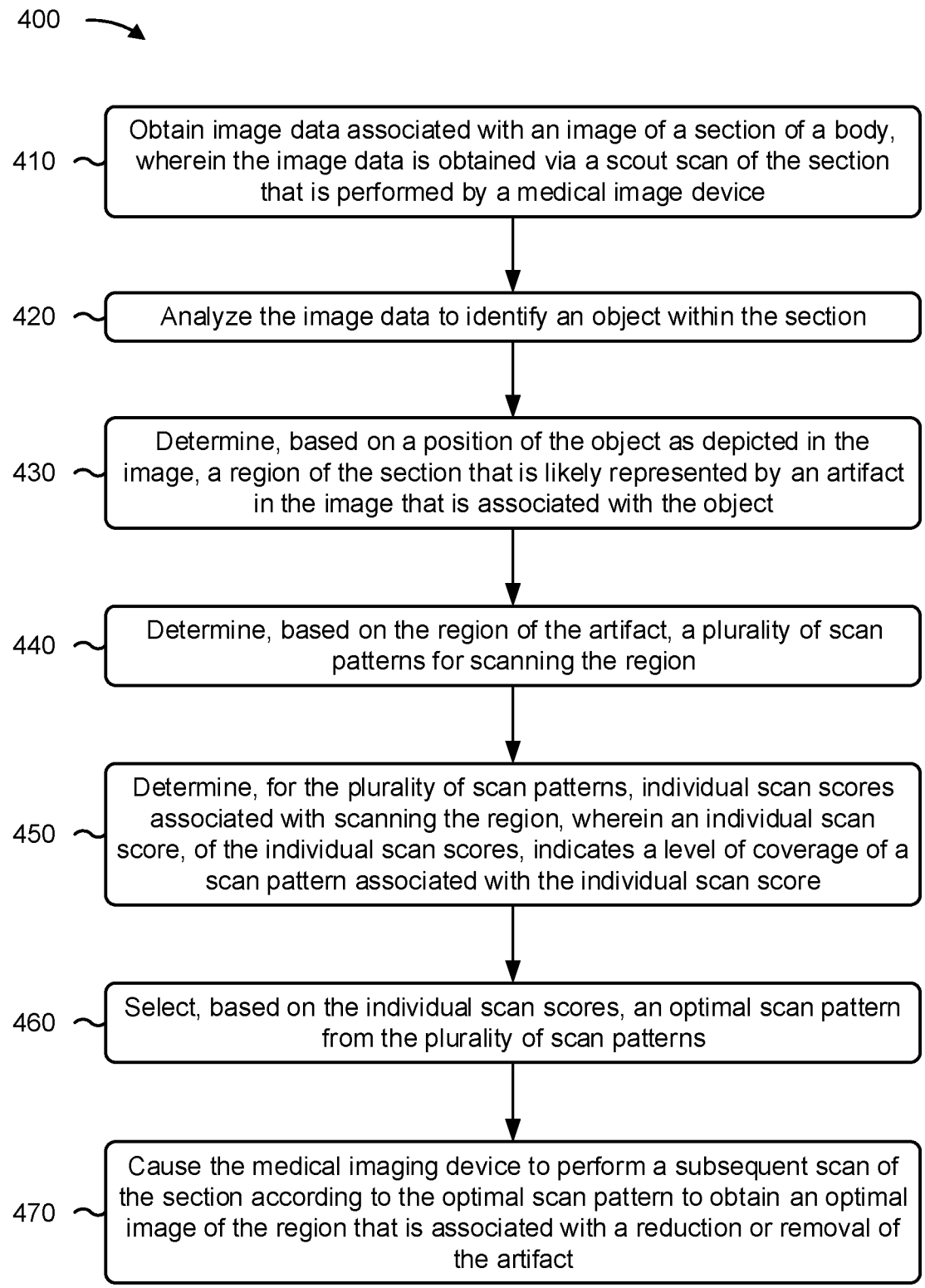
FIGS. 4-6 are flowcharts of example processes relating to an optimal scan pattern for a medical imaging device.

FIG. 4 is a flowchart of an example process 400 associated with an optimal scan pattern for medical imaging device. In some implementations, one or more process blocks of FIG. 4 may be performed by a scan optimization system (e.g., scan optimization system 201). In some implementations, one or more process blocks of FIG. 4 may be performed by another device or a group of devices separate from or including the scan optimization system, such as a medical imaging device (e.g., medical imaging device 230), and/or a user device (e.g., user device 250). Additionally, or alternatively, one or more process blocks of FIG. 4 may be performed by one or more components of device 300, such as processor 320, memory 330, storage component 340, input component 350, output component 360, and/or communication interface 370.

As shown in FIG. 4, process 400 may include obtaining image data associated with an image of a section of a body, wherein the image data is obtained via a scout scan of the section that is performed by a medical image device (block 410). For example, the scan optimization system may obtain image data associated with an image of a section of a body, as described above. In some implementations, the image data is obtained via a scout scan of the section that is performed by a medical image device.

As further shown in FIG. 4, process 400 may include analyzing the image data to identify an object within the section (block 420). For example, the scan optimization system may analyze the image data to identify an object within the section, as described above.

As further shown in FIG. 4, process 400 may include determining, based on a position of the object as depicted in the image, a region of the section that is likely represented by an artifact in the image that is associated with the object (block 430). For example, the scan optimization system may determine, based on a position of the object as depicted in the image, a region of the section that is likely represented by an artifact in the image that is associated with the object, as described above.

As further shown in FIG. 4, process 400 may include determining, based on the region of the artifact, a plurality of scan patterns for scanning the region (block 440). For example, the scan optimization system may determine, based on the region of the artifact, a plurality of scan patterns for scanning the region, as described above.

As further shown in FIG. 4, process 400 may include determining, for the plurality of scan patterns, individual scan scores associated with scanning the region, wherein an individual scan score, of the individual scan scores, indicates a level of coverage of a scan pattern associated with the individual scan score (block 450). For example, the scan optimization system may determine, for the plurality of scan patterns, individual scan scores associated with scanning the region, as described above. In some implementations, an individual scan score, of the individual scan scores, indicates a level of coverage of a scan pattern associated with the individual scan score.

As further shown in FIG. 4, process 400 may include selecting, based on the individual scan scores, an optimal scan pattern from the plurality of scan patterns (block 460). For example, the scan optimization system may select, based on the individual scan scores, an optimal scan pattern from the plurality of scan patterns, as described above.

As further shown in FIG. 4, process 400 may include causing the medical imaging device to perform a subsequent scan of the section according to the optimal scan pattern to obtain an optimal image of the region that is associated with a reduction or removal of the artifact (block 470). For example, the scan optimization system may cause the medical imaging device to perform a subsequent scan of the section according to the optimal scan pattern to obtain an optimal image of the region that is associated with a reduction or removal of the artifact, as described above.

Process 400 may include additional implementations, such as any single implementation or any combination of implementations described below and/or in connection with one or more other processes described elsewhere herein.

In a first implementation, analyzing the image data comprises using an image processing technique to analyze the image data, wherein the image processing technique is configured to identify one or more types of objects in images based on at least one of: pixel values that are used to depict the one or more types of objects, locations of the one or more types of objects, shapes of the one or more types of objects, or sizes of the one or more types of objects.

In a second implementation, determining the region of the section comprises determining, based on analyzing the image data, an anatomical characteristic of the section, locations of the region within the section, and an object characteristic of the object, and using a machine learning model to determine the region based on the anatomical characteristic, the location of the region within the section, and the object characteristic of the object, wherein the machine learning model was trained based on historical images of bodies that include one or more objects and artifacts generated based on the bodies including the one or more objects.

In a third implementation, determining the plurality of scan patterns comprises determining the position of the object, determining a characteristic of the section, determining scan settings associated with a scanner of the medical imaging device performing a subsequent scan of the section, and generating respective sets of scan trajectories of the scanner for the plurality of scans based on the position of the object, the characteristic of the section, and the scan settings.

In a fourth implementation, the artifact is one artifact of a plurality of artifacts in the image, wherein the region is associated with locations of the section that are likely represented by the plurality of artifacts in the image.

In a fifth implementation, determining the individual scan scores comprises, for a scan pattern of the plurality of scan patterns, identifying locations of the region, determining a percentage of the locations that are included in at least one scan plane of a trajectory of the scan pattern, and determining a scan score for the scan pattern based on the percentage of the locations.

In a sixth implementation, selecting the optimal scan pattern comprises identifying, from the individual scan scores, an optimal scan score that indicates that a largest percentage of the region is included in at least one scan plane of a trajectory of a scan pattern associated with the optimal scan score, and designating the scan pattern as the optimal scan pattern.

In a seventh implementation, the medical imaging device comprises a computed tomography (CT) scanner, and a robotic arm that supports the CT scanner and is configured to permit the medical imaging device to move the CT scanner in one or more non-circular trajectories of the optimal scan pattern to obtain the optimized image data.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
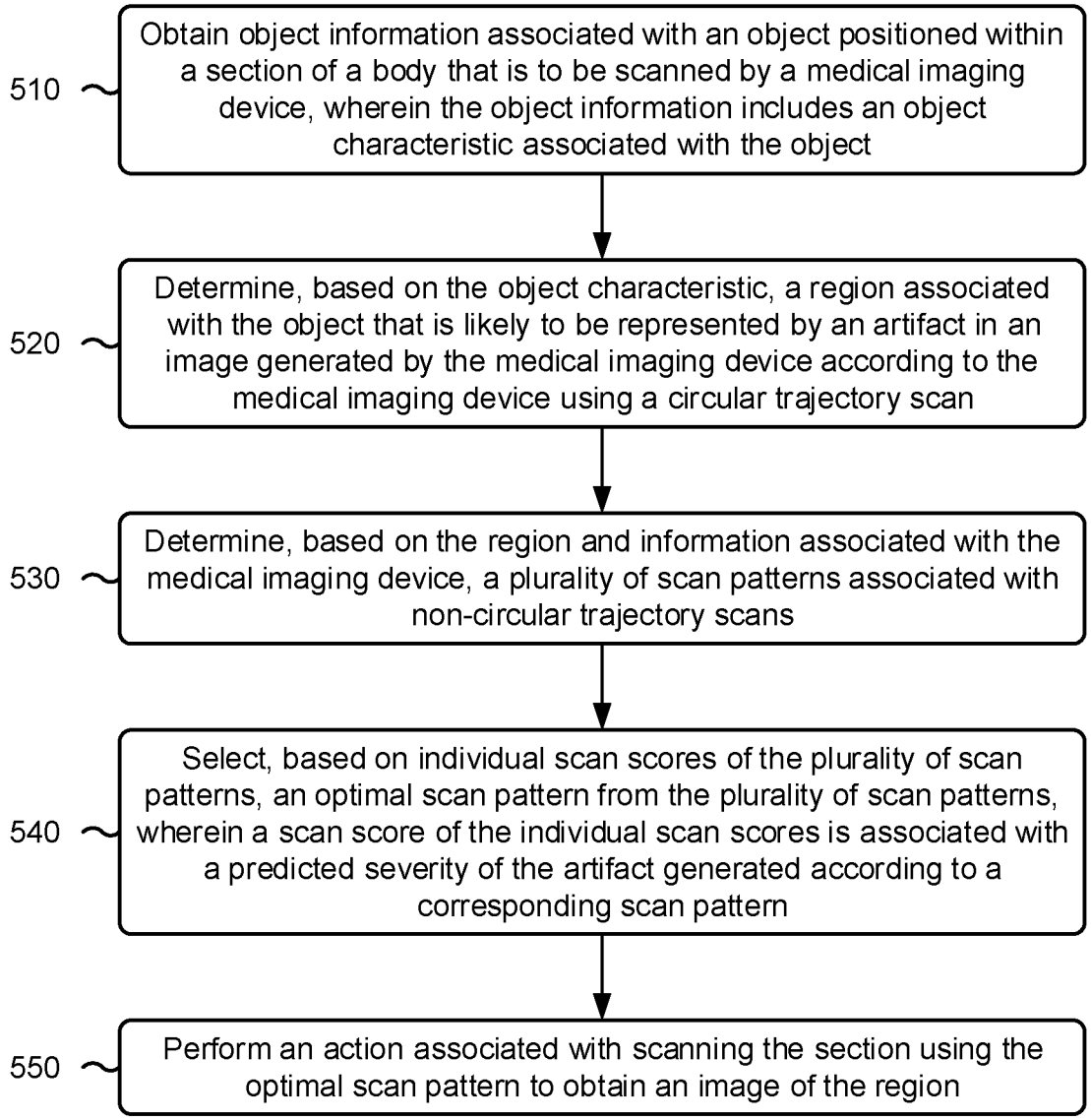

FIG. 5 is a flowchart of an example process 500 associated with an optimal scan pattern for medical imaging device. In some implementations, one or more process blocks of FIG. 5 may be performed by a scan optimization system (e.g., scan optimization system 201). In some implementations, one or more process blocks of FIG. 5 may be performed by another device or a group of devices separate from or including the scan optimization system, such as a medical imaging device (e.g., medical imaging device 230), and/or a user device (e.g., user device 250). Additionally, or alternatively, one or more process blocks of FIG. 5 may be performed by one or more components of device 300, such as processor 320, memory 330, storage component 340, input component 350, output component 360, and/or communication interface 370.

As shown in FIG. 5, process 500 may include obtaining object information associated with an object positioned within a section of a body that is to be scanned by a medical imaging device, wherein the object information includes an object characteristic associated with the object (block 510). For example, the scan optimization system may obtain object information associated with an object positioned within a section of a body that is to be scanned by a medical imaging device, as described above. In some implementations, the object information includes an object characteristic associated with the object.

As further shown in FIG. 5, process 500 may include determining, based on the object characteristic, a region associated with the object that is likely to be represented by an artifact in an image generated by the medical imaging device according to the medical imaging device using a circular trajectory scan (block 520). For example, the scan optimization system may determine, based on the object characteristic, a region associated with the object that is likely to be represented by an artifact in an image generated by the medical imaging device according to the medical imaging device using a circular trajectory scan, as described above.

As further shown in FIG. 5, process 500 may include determining, based on the region and information associated with the medical imaging device, a plurality of scan patterns associated with non-circular trajectory scans (block 530). For example, the scan optimization system may determine, based on the region and information associated with the medical imaging device, a plurality of scan patterns associated with non-circular trajectory scans, as described above.

As further shown in FIG. 5, process 500 may include selecting, based on individual scan scores of the plurality of scan patterns, an optimal scan pattern from the plurality of scan patterns, wherein a scan score of the individual scan scores is associated with a predicted severity of the artifact that is generated according to a corresponding scan pattern used to scan the region (block 540). For example, the scan optimization system may select, based on individual scan scores of the plurality of scan patterns, an optimal scan pattern from the plurality of scan patterns, as described above. In some implementations, a scan score of the individual scan scores is associated with a predicted severity of the artifact that is generated according to a corresponding scan pattern used to scan the region. In some implementations, the scan score indicates an amount of the region that a corresponding scan pattern is capable of scanning via scan planes that do not intersect the object.

As further shown in FIG. 5, process 500 may include performing an action associated with scanning the section using the optimal scan pattern to obtain an image of the region (block 550). For example, the scan optimization system may perform an action associated with scanning the section using the optimal scan pattern to obtain an image of the region, as described above.

Process 500 may include additional implementations, such as any single implementation or any combination of implementations described below and/or in connection with one or more other processes described elsewhere herein.

In a first implementation, the object characteristic of the object includes at least one of a position of the object within the section, a material of the object, a type of the object, a size of the object, or a shape of the object.

In a second implementation, the object information is obtained based on an analysis of image data associated with a scout scan performed by the medical imaging device, wherein the medical imaging device used the circular trajectory scan for the scout scan.

In a third implementation, the information associated with the medical imaging device includes at least one of information that identifies a frame rate of a scanner of the medical imaging device, information that identifies a resolution of the scanner, or information that identifies trajectory limitations of the scanner.

In a fourth implementation, process 500 includes providing, via a user interface, information associated with the optimal scan pattern, or transmitting the optimal scan pattern to the medical imaging device to cause the medical imaging device to perform a scan according to the optimal scan pattern.

In a fifth implementation, the medical imaging device comprises a computed tomography (CT) scanner, and a robotic arm that supports the CT scanner and is configured to permit the medical imaging device to move the CT scanner in one or more non-circular trajectories associated with a non-circular trajectory scan.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
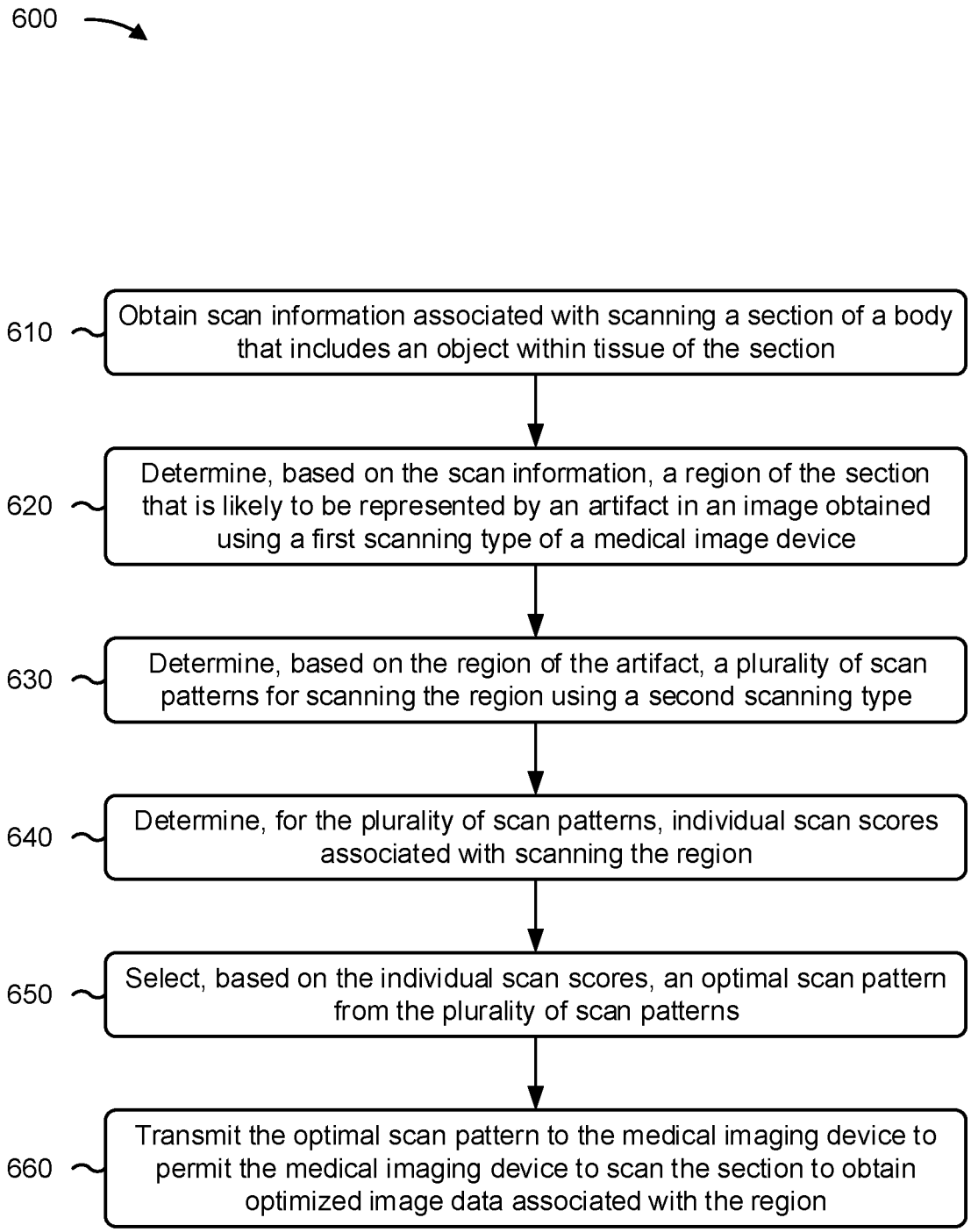

FIG. 6 is a flowchart of an example process 600 associated with an optimal scan pattern for medical imaging device. In some implementations, one or more process blocks of FIG. 6 may be performed by a scan optimization system (e.g., scan optimization system 201). In some implementations, one or more process blocks of FIG. 6 may be performed by another device or a group of devices separate from or including the scan optimization system, such as a medical imaging device (e.g., medical imaging device 230), and/or a user device (e.g., user device 250). Additionally, or alternatively, one or more process blocks of FIG. 6 may be performed by one or more components of device 300, such as processor 320, memory 330, storage component 340, input component 350, output component 360, and/or communication interface 370.

As shown in FIG. 6, process 600 may include obtaining scan information associated with scanning a section of a body that includes an object within tissue of the section (block 610). For example, the scan optimization system may obtain scan information associated with scanning a section of a body that includes an object within tissue of the section, as described above.

As further shown in FIG. 6, process 600 may include determining, based on the scan information, a region of the section that is likely to be represented by an artifact in an image obtained using a first scanning type of a medical image device (block 620). For example, the scan optimization system may determine, based on the scan information, a region of the section that is likely to be represented by an artifact in an image obtained using a first scanning type of a medical image device, as described above.

As further shown in FIG. 6, process 600 may include determining, based on the region of the artifact, a plurality of scan patterns for scanning the region using a second scanning type (block 630). For example, the scan optimization system may determine, based on the region of the artifact, a plurality of scan patterns for scanning the region using a second scanning type, as described above.

As further shown in FIG. 6, process 600 may include determining, for the plurality of scan patterns, individual scan scores associated with scanning the region (block 640). For example, the scan optimization system may determine, for the plurality of scan patterns, individual scan scores associated with scanning the region, as described above.

As further shown in FIG. 6, process 600 may include selecting, based on the individual scan scores, an optimal scan pattern from the plurality of scan patterns (block 650). For example, the scan optimization system may select, based on the individual scan scores, an optimal scan pattern from the plurality of scan patterns, as described above.

As further shown in FIG. 6, process 600 may include transmitting the optimal scan pattern to the medical imaging device to permit the medical imaging device to scan the section to obtain optimized image data associated with the region (block 660). For example, the scan optimization system may transmit the optimal scan pattern to the medical imaging device to permit the medical imaging device to scan the section to obtain optimized image data associated with the region, as described above.

Process 600 may include additional implementations, such as any single implementation or any combination of implementations described below and/or in connection with one or more other processes described elsewhere herein.

In a first implementation, the scan information includes body information associated with the section and object information associated with the object, wherein the region of the section is determined based on at least one of: an anatomy of the section identified in the body information, a dimension of the section identified in the body information, a location of the object within the section identified in the object information, a material of the object identified in the object information, a type of the object identified in the object information, a size of the object identified in the object information, or a shape of the object identified in the object information.

In a second implementation, the plurality of scan patterns are determined based on at least one of an anatomy of the section that is identified in the scan information, a dimension of the section that is identified in the scan information, trajectory limitations of a scanner of the medical imaging device that is identified in the scan information, or a setting of the scanner for scanning the section that is identified in the scan information.

In a third implementation, the first scanning type is associated with a scanner of the medical imaging device using a circular scan trajectory and the second scanning type is associated with the scanner of the medical imaging device using a non-circular scan trajectory.

In a fourth implementation, the individual scan scores are associated with percentages of the region that are included in a scan plane, of trajectories of the plurality of scan patterns, that does not include the object.

In a fifth implementation, process 600 includes selecting the optimal scan pattern being associated with a scan score that indicates that the optimal scan pattern includes trajectories that provide scan planes that are configured to cover a largest portion of the region, relative to the plurality of scan patterns, without including the object.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise form disclosed. Modifications and variations may be made in light of the above disclosure or may be acquired from practice of the implementations.

As used herein, the term "component" is intended to be broadly construed as hardware, firmware, or a combination of hardware and software.

As used herein, satisfying a threshold may, depending on the context, refer to a value being greater than the threshold, greater than or equal to the threshold, less than the threshold, less than or equal to the threshold, equal to the threshold, etc., depending on the context.

It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
    obtaining, by a device, image data associated with an image of a section of a body,
        wherein the image data is obtained via a scout scan of the section that is performed by a medical image device;
    analyzing, by the device, the image data to identify an object within the section;
    determining, by the device and based on a position of the object as depicted in the image, a region of the section that is likely represented by an artifact in the image that is associated with the object;
    determining, by the device and based on the region of the artifact, a plurality of scan patterns for scanning the region;
    determining, by the device and for the plurality of scan patterns, individual scan scores associated with scanning the region,
        wherein an individual scan score, of the individual scan scores, indicates a level of coverage of a scan pattern associated with the individual scan score;
    selecting, by the device and based on the individual scan scores, an optimal scan pattern from the plurality of scan patterns; and
    causing, by the device, the medical imaging device to perform a subsequent scan of the section according to the optimal scan pattern to obtain an optimal image of the region that is associated with a reduction or removal of the artifact.

2. The method of claim 1, wherein analyzing the image data comprises:
    using an image processing technique to analyze the image data, wherein the image processing technique is configured to identify one or more types of objects in images based on at least one of:
        pixel values that are used to depict the one or more types of objects,
        locations of the one or more types of objects,
        shapes of the one or more types of objects, or
        sizes of the one or more types of objects.

3. The method of claim 1, wherein determining the region of the section comprises:
    determining, based on analyzing the image data, an anatomical characteristic of the section, locations of the region within the section, and an object characteristic of the object; and
    using a machine learning model to determine the region based on the anatomical characteristic, the location of the region within the section, and the object characteristic of the object,
        wherein the machine learning model was trained based on historical images of bodies that include one or more objects and artifacts generated based on the bodies including the one or more objects.

4. The method of claim 1, wherein determining the plurality of scan patterns comprises:
    determining the position of the object;
    determining a characteristic of the section;
    determining scan settings associated with a scanner of the medical imaging device performing the subsequent scan of the section; and
    generating respective sets of scan trajectories of the scanner for the plurality of scans patterns based on the position of the object, the characteristic of the section, and the scan settings.

5. The method of claim 1, wherein the artifact is one artifact of a plurality of artifacts in the image,
    wherein the region is associated with locations of the section that are likely represented by the plurality of artifacts in the image.

6. The method of claim 1, wherein determining the individual scan scores comprises:
    for a scan pattern of the plurality of scan patterns:
        identifying locations of the region;
        determining a percentage of the locations that are included in at least one scan plane of a trajectory of the scan pattern; and
        determining a scan score for the scan pattern based on the percentage of the locations.

7. The method of claim 1, wherein selecting the optimal scan pattern comprises:
    identifying, from the individual scan scores, an optimal scan score that indicates that a largest percentage of the region is included in at least one scan plane of a trajectory of a scan pattern associated with the optimal scan score; and
    designating the scan pattern as the optimal scan pattern.

8. The method of claim 1, wherein the medical imaging device comprises:
    a computed tomography (CT) scanner; and
    a robotic arm that supports the CT scanner and is configured to permit the medical imaging device to move the CT scanner in one or more non-circular trajectories of the optimal scan pattern to obtain the optimal image.

9. A non-transitory computer-readable medium storing a set of instructions, the set of instructions comprising:
    one or more instructions that, when executed by one or more processors of a device, cause the device to:
        obtain object information associated with an object positioned within a section of a body that is to be scanned by a medical imaging device, wherein the object information includes an object characteristic associated with the object;
determine, based on the object characteristic, a region associated with the object that is likely to be represented by an artifact in an image generated by the medical imaging device according to the medical imaging device using a circular trajectory scan;
determine, based on the region and information associated with the medical imaging device, a plurality of scan patterns associated with non-circular trajectory scans;
select, based on individual scan scores of the plurality of scan patterns, an optimal scan pattern from the plurality of scan patterns,
wherein a scan score of the individual scan scores is associated with a predicted severity of the artifact generated according to a corresponding scan pattern used to scan the region; and
perform an action associated with scanning the section using the optimal scan pattern to obtain an image of the region.

10. The non-transitory computer-readable medium of claim 9, wherein the object characteristic of the object includes at least one of:
a position of the object within the section;
a material of the object;
a type of the object;
a size of the object; or
a shape of the object.

11. The non-transitory computer-readable medium of claim 9, wherein the object information is obtained based on an analysis of image data associated with a scout scan performed by the medical imaging device,
wherein the medical imaging device used the circular trajectory scan for the scout scan.

12. The non-transitory computer-readable medium of claim 9, wherein the information associated with the medical imaging device includes at least one of:
information that identifies a frame rate of a scanner of the medical imaging device;
information that identifies a resolution of the scanner; or
information that identifies trajectory limitations of the scanner.

13. The non-transitory computer-readable medium of claim 9, wherein the one or more instructions, that cause the device to perform an action associated with scanning the section, cause the device to:
provide, via a user interface, information associated with the optimal scan pattern; or
transmit the optimal scan pattern to the medical imaging device to cause the medical imaging device to perform a scan according to the optimal scan pattern.

14. The non-transitory computer-readable medium of claim 9, wherein the medical imaging device comprises:
a computed tomography (CT) scanner; and
a robotic arm that supports the CT scanner and is configured to permit the medical imaging device to move the CT scanner in one or more non-circular trajectories associated with a non-circular trajectory scan.

15. A device, comprising:
one or more memories; and
one or more processors, communicatively coupled to the one or more memories, configured to:
obtain scan information associated with scanning a section of a body that includes an object within tissue of the section;
determine, based on the scan information, a region of the section that is likely to be represented by an artifact in an image obtained using a first scanning type of a medical image device;
determine, based on the region of the artifact, a plurality of scan patterns for scanning the region using a second scanning type;
determine for the plurality of scan patterns, individual scan scores associated with scanning the region;
select, based on the individual scan scores, an optimal scan pattern from the plurality of scan patterns; and
transmit the optimal scan pattern to the medical imaging device to permit the medical imaging device to scan the section to obtain optimized image data associated with the region.

16. The device of claim 15, wherein the scan information includes body information associated with the section and object information associated with the object,
wherein the region of the section is determined based on at least one of:
an anatomy of the section identified in the body information;
a dimension of the section identified in the body information;
a location of the object within the section identified in the object information;
a material of the object identified in the object information;
a type of the object identified in the object information;
a size of the object identified in the object information; or
a shape of the object identified in the object information.

17. The device of claim 15, wherein the plurality of scan patterns are determined based on at least one of:
an anatomy of the section that is identified in the scan information;
a dimension of the section that is identified in the scan information;
trajectory limitations of a scanner of the medical imaging device that is identified in the scan information; or
a setting of the scanner for scanning the section that is identified in the scan information.

18. The device of claim 15, wherein the first scanning type is associated with a scanner of the medical imaging device using a circular scan trajectory and the second scanning type is associated with the scanner of the medical imaging device using a non-circular scan trajectory.

19. The device of claim 15, wherein the individual scan scores, are associated with percentages of the region that are included in a scan plane, of trajectories of the plurality of scan patterns, that does not include the object.

20. The device of claim 15, wherein the one or more processors, when selecting the optimal scan pattern, are configured to:
select the optimal scan pattern being associated with a scan score that indicates that the optimal scan pattern includes trajectories that provide scan planes that are configured to cover a largest portion of the region, relative to the plurality of scan patterns, without including the object.

* * * * *